(12) United States Patent
Soutorine et al.

(10) Patent No.: US 11,259,822 B2
(45) Date of Patent: Mar. 1, 2022

(54) DEVICE FOR RETRIEVING A BODY FROM A TUBULAR STRUCTURE

(75) Inventors: Mikhail Soutorine, Oakleigh (AU); Artem Nikolaevich Chernov-Haraev, Moscow (RU); Sergei Dmitrievich Prokoshkin, Moscow (RU); Elena Prokopievna Ryklina, Moscow (RU); Irina Yurievna Khmelevskaya, Moscow (RU); Andrey Victorovich Korotitskiy, Moscow (RU); Rouslan Valereevich Ipatkin, Moscow (RU)

(73) Assignees: GLOBETEK 2000 PTY LTD, Brighton (AU); The Federal State Autonomous Educational Institution of The Higher Professional Education "National University of Science and Technology 'MISIS'", Moscow (RU)

( * ) Notice: Subject to any disclaimer, the term of this patent is extended or adjusted under 35 U.S.C. 154(b) by 64 days.

(21) Appl. No.: 13/990,638

(22) PCT Filed: Nov. 30, 2011

(86) PCT No.: PCT/AU2011/001561
§ 371 (c)(1),
(2), (4) Date: Nov. 14, 2013

(87) PCT Pub. No.: WO2012/071620
PCT Pub. Date: Jun. 7, 2012

(65) Prior Publication Data
US 2014/0066948 A1 Mar. 6, 2014

(30) Foreign Application Priority Data
Nov. 30, 2010 (RU) .......................... RU2010/000711

(51) Int. Cl.
*A61B 17/22* (2006.01)
*A61B 17/50* (2006.01)
(Continued)

(52) U.S. Cl.
CPC ...... *A61B 17/22031* (2013.01); *A61B 17/221* (2013.01); *A61B 17/50* (2013.01);
(Continued)

(58) Field of Classification Search
CPC . A61B 17/22; A61B 17/221; A61B 17/22031; A61B 17/22038;
(Continued)

(56) References Cited

U.S. PATENT DOCUMENTS 3,500,820 A 3/1970 Almen
4,706,671 A * 11/1987 Weinrib ............... A61B 17/221
606/159
(Continued)

FOREIGN PATENT DOCUMENTS

EP 2 399 525 A1 12/2011
JP 11-47141 2/1999
(Continued)

OTHER PUBLICATIONS

PCT Written Opinion for International Application No. PCT/AU2011/001561, date of completion Feb. 10, 2012, 13 pages.
(Continued)

*Primary Examiner* — Wade Miles
*Assistant Examiner* — Mikail A Mannan
(74) *Attorney, Agent, or Firm* — Crowell & Moring LLP

(57) ABSTRACT

Some embodiments relate to a device for retrieving a body from within a tubular structure, the device having a proximal end and a distal end and comprising: a device body at the proximal end; a conduit extending away from the device body to the distal end and sized to be receivable in the
(Continued)

tubular structure; at least one actuator operably associated with the device body; a first strand extending at least in part through the conduit; a second strand extending at least in part through the conduit; wherein the first and second strands are affixed at the distal end of the device, and wherein the second strand is wound around the first strand along at least a distal length of the first strand; wherein the at least one actuator is operable to cause the second strand to adopt an expanded state in which the second strand defines a trawl volume to catch the body for retrieval of the body from the tubular structure.

21 Claims, 5 Drawing Sheets

(51) Int. Cl.
 *A61B 17/221* (2006.01)
 *A61M 5/00* (2006.01)
 *A61B 17/00* (2006.01)
(52) U.S. Cl.
 CPC .............. *A61B 2017/00867* (2013.01); *A61B 2017/2212* (2013.01); *A61B 2017/2217* (2013.01); *A61B 2017/22082* (2013.01); *A61M 5/007* (2013.01)
(58) Field of Classification Search
 CPC ........ A61B 17/22045; A61B 17/22047; A61B 17/22049; A61B 17/32056; A61B 17/26; A61B 2017/2212; A61B 2017/2215; A61B 2017/2217; A61B 2017/00318; A61B 2017/00323; A61B 2017/00327; A61F 2/95; A61F 2002/9517; A61F 2/013
 USPC .................. 606/110–115, 127, 200; 623/1.11
 See application file for complete search history.

(56) References Cited

U.S. PATENT DOCUMENTS

| | | | | |
|---|---|---|---|---|
| 5,171,314 | A * | 12/1992 | Dulebohn | A61B 17/32056 606/110 |
| 5,527,326 | A * | 6/1996 | Hermann | A61B 17/221 606/159 |
| 6,190,394 | B1 * | 2/2001 | Lind | A61B 17/221 606/127 |
| 6,258,101 | B1 | 7/2001 | Blake, III | |
| 6,511,492 | B1 * | 1/2003 | Rosenbluth | A61B 17/221 606/159 |
| 2001/0031981 | A1 * | 10/2001 | Evans | A61B 17/221 606/200 |
| 2004/0073243 | A1 | 4/2004 | Sepetka et al. | |
| 2004/0153095 | A1 * | 8/2004 | Seddon | A61B 17/221 606/113 |
| 2004/0243023 | A1 * | 12/2004 | Grigoryants | A61B 10/04 600/564 |
| 2006/0173468 | A1 * | 8/2006 | Simmon | A61B 17/06109 606/113 |
| 2006/0224177 | A1 | 10/2006 | Finitsis | |
| 2007/0260266 | A1 * | 11/2007 | Karpiel | A61B 17/221 606/127 |
| 2008/0262487 | A1 * | 10/2008 | Wensel | A61B 17/221 606/27 |
| 2010/0016832 | A1 * | 1/2010 | Thai | A61M 25/0021 604/508 |
| 2010/0036410 | A1 * | 2/2010 | Krolik | A61B 17/22032 606/194 |

FOREIGN PATENT DOCUMENTS

| | | |
|---|---|---|
| JP | 2001-507598 A | 6/2001 |
| JP | 2003-33359 | 2/2003 |
| RU | 2 145 488 C1 | 5/1998 |
| WO | WO 97/27808 A1 | 8/1997 |
| WO | WO 98/29043 A1 | 7/1998 |
| WO | WO 02/055146 A1 | 7/2002 |
| WO | WO 2009/150920 A1 | 12/2009 |
| WO | WO 2010/095712 A1 | 8/2010 |
| WO | WO 2011/011765 A2 | 1/2011 |

OTHER PUBLICATIONS

PCT International Search Report for International Application No. PCT/AU2011/001561, date of completion Feb. 10, 2012, 7 pages.
PCT International Preliminary Report on Patentability for International Application No. PCT/AU2011/001561, dated Jun. 4, 2013, 14 pages.
Office Action dated Jun. 21, 2016, for corresponding Japanese Application No. 2013-541151.

* cited by examiner

DEVICE FOR RETRIEVING A BODY FROM A TUBULAR STRUCTURE

CROSS-REFERENCE TO RELATED APPLICATIONS

This application is a National Stage application of PCT International Application No. PCT/AU2011/001561, filed 30 Nov. 2011, which claims priority to PCT International Application Number No. PCT/RU2010/000711, filed 30 Nov. 2010, the entire contents of which is explicitly hereby incorporated by reference as if it were written herein.

TECHNICAL FIELD

Described embodiments generally relate to a device for retrieving a body from a tubular structure. For example, the device may be used to retrieve an unwanted foreign or organic body within a tubular organ in a human or animal. Embodiments relate to the field of medical devices, specifically to devices meant for retrieving foreign bodies, more specifically, the stones from the ureter or bile duct.

BACKGROUND

A surgical instrument for the extraction of concrements from tubular organs, specifically stones from the ureter or bile duct, equipped with a manipulator for moving, opening, closing and deploying a special wire trap exists (U.S. Pat. No. 6,258,101, published Oct. 7, 2001).

This device includes an elongated frame for deploying surgical tools such as snares and baskets. A hinge mechanism to rotate the output shaft is mounted at the end of the frame. Holes for the fingers, located at the end of the handle as well as on the hinge mechanism, allow for manipulation of the device with one hand. A linear movement of a hinged mechanism is used to move of the output shaft and the basket, while the rotation of the shaft is achieved by the turning of the hinge mechanism from side to side relative to the direction of the straight-line motion. The device is designed in such a way that the output shaft can rotate in all positions in a straight-line motion. This surgical device is capable of simultaneous rotation and reciprocal step-by-step motion of the output shaft and the basket allowing for precise manipulation of the surgical unit.

Another invention is a device for extracting stones from the tubular cavities with a frame, a sleeve, a flexible tube and a carrying cable with a catching basket, and a handle (RU 2061420 published Oct. 6, 1996).

The handle is made in the form of a rod with calibrated feed marks and wedge-shaped groove established in the frame. The sleeve is pulled onto the handle and comes with a groove-oriented window. The end of the elastic tube is connected to the frame via a nut with an elastic sleeve. In order to connect a carrying cable with the handle, the end of the cable is passed through the wedge-shaped groove of the handle until it exits through the window of the sleeve. By applying force to the handle, the end of the sleeve squeezes a calibrated spring mounted in the hole of the frame. This motion moves the sleeve along the groove and clamps the cable in the window, applying a force that is capped at a certain level. The opening of the basket is fixed at a required level via clamping the screw of the handle to the frame.

The disadvantage of the above mentioned analogous devices is that their manipulators (handles) are designed to control basket or hinge-type traps, the working parts of which are mounted on the same cable and do not allow for separate manipulation of individual parts of the trap.

The closest device to the proposed invention is a "Trawl" for extracting foreign bodies from the tubular organs (RU 2145488, published Feb. 20, 2002). The device includes a manipulator, which contains a hollow cylindrical cup with an axial hole at the hollow end of the manipulator and a connection on the outer surface of that end. A catheter is connected to the end of this connection. The device also has a sleeve, coaxially located in a cylindrical cup: the sleeve has a groove on its outer surface and the shoulder with a hole allowing to fix the spiral-shaped wire on one of the ends. Another element of the device is a rod located in the sleeve, coaxial with its longitudinal axis, one end of which is tightly connected with a straight wire, and the opposite end is equipped with handle to control the working part of the device. The manipulator is capable of fixing the sleeve on the cylindrical cup as well as fixing the rod on the sleeve.

This device allows for independent manipulation of the wires, however it has a significant shortcoming, which is as follows.

When working with a manipulator a surgeon feels uncomfortable as he needs to lock and unlock the sleeve. This motion requires both of his hands. At the same time all modern manipulators (such as those mentioned above) are designed in a way that the second hand can be free. In this case, the outcome of the operation often depends on the responsiveness of a surgeon: in specific situations time lost in handling the device can lead to irreversible consequences. Therefore, the manipulation of this device requires special training Clinical experience illustrates that the device is quite complicated to use.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF SUMMARY

Some embodiments relate to a device for retrieving a body from within a tubular structure, the device having a proximal end and a distal end and comprising:
   a device body at the proximal end;
   a conduit extending away from the device body to the distal end and sized to be receivable in the tubular structure;
   at least one actuator operably associated with the device body;
   a first strand extending at least in part through the conduit;
   a second strand extending at least in part through the conduit;
   wherein the first and second strands are affixed at the distal end of the device, and wherein the second strand is wound around the first strand along at least a distal length of the first strand;
   wherein the at least one actuator is operable to cause the second strand to adopt an expanded state in which the second strand defines a trawl volume to catch the body for retrieval of the body from the tubular structure.

The trawl volume may be defined by a spiral shape of the second strand in the expanded state. The trawl volume may taper inwardly toward the first strand in a direction toward the distal end. The second strand may be formed of a shape-memory alloy along at least a distal length of the second strand. The distal length of the second strand may be formed to have a shape memory that defines the trawl volume.

In the expanded state, the second strand may extend radially beyond an outside diameter of the conduit. The at least one actuator may be operable to cause the second strand to adopt a contracted state in which the second strand extends radially adjacent the first strand. The first strand may have a larger diameter and stiffness than a diameter and stiffness of the second strand.

The device may further comprise a distal tip sleeve located at a distal extremity of the device, the distal tip sleeve receiving distal ends of the first and second strands, wherein the distal tip sleeve has a diameter greater than or equal to a diameter of the conduit. The distal tip sleeve may retain the distal ends of the first and second strands in fixed relation to each other by clamping or crimping them together. The distal tip sleeve may have a rounded external profile.

The at least one actuator may be operable to cause the first and second strands to adopt a retracted state in which distal lengths of the first and second strands are substantially enclosed within the conduit, wherein in the retracted state, the conduit obstructs the second strand from adopting the expanded state.

The at least one actuator may be operable to cause the first and second strands to adopt an extended state in which distal lengths of the first and second strands are substantially uncovered by the conduit, wherein in the extended state, the conduit does not obstruct the second strand from adopting the expanded state.

The at least one actuator may include first and second actuators. The first and second actuators may be separately operable. The first strand may be coupled to the first actuator and the second strand may be coupled to the second actuator, whereby relative movement between the first and second actuators causes relative movement between the first and second strands. The second strand is caused to adopt the expanded state in response to relative movement between the first and second actuators.

The at least one actuator may be moveable relative to the device body and may have at least one engagement portion to engage with at least one complementary structure of the device body, such that when the at least one engagement portion is engaged with the at least one complementary structure, the at least one actuator tends to be retained in place relative to the device body. The at least one engagement portion and the at least one complementary structure may comprise a resiliently deflectable portion and a mating socket, wherein manual force can be applied to remove the resiliently deflectable portion from the mating socket.

The at least one actuator may be slidably moveable relative to the device body. The at least one actuator may be slidably movable in an axial direction to cause axial movement of at least one of the first strand and the second strand.

The conduit may define a lumen within which the first and second strands extend, the lumen and the first and second strands being sized to allow flow of fluid through the lumen toward the distal end. The device may further comprise a fluid inlet arranged on the device body, the fluid inlet in fluid communication with the lumen to allow contrast fluid to be passed from the fluid inlet to the distal end via the lumen.

The conduit may be sized to be receivable within an instrument channel of an endoscope. The first and second strands may be metallic strands formed of bio-compatible materials.

Some embodiments also relate to use of the described device to retrieve a body from a tubular structure.

Some embodiments relate to a device "Trawl" for retrieving of foreign bodies from tubular organs, which includes:
a manipulator;
an adapter is installed at the output end of a frame of the manipulator;
a connector is mounted on the input end of the adapter;
a feeder of contrast fluid is joined to the connector;
a flexible catheter is fixed to an output end of the adapter;
an axial and screw wire are located inside the frame of the manipulator and the flexible catheter; these wires are made of a shape memory alloy and are able to move along a guide axis; a frontal end of these wires is fixed on control sliders and the opposed distal ends are fixed on a cylindrical tip-sleeve, this sleeve is mounted outside a free end of the flexible catheter; wherein the control sliders, located in the frame, are able to move and fix jointly or independently relative to the guide axis of the frame.

The axial wire may be located inside a cone formed by the spiral wire, both located inside the elastic catheter. The spiral and axial wires may be made of nitinol. The mechanism of moving and fixing the slider control may be executed in the form of two spring-loaded balls, set symmetrically to the guide axis of the frame, and a pair of grooves made on inner walls of the frame.

The distal ends of the spiral and axial wires may be mounted in a longitudinal channel of the cylindrical tip-sleeve via pressure crimping. The distal ends of the spiral and axial wires may be mounted in a longitudinal channel of the cylindrical tip-sleeve by pressure crimping in a temperature range of direct martensitic transformation inside both wires' material.

The longitudinal distance between the turns of the spiral wire may not exceed the radius of the adjacent turns. The outer diameter of the cylindrical tip-sleeve may be at least equal to an inner diameter of the flexible catheter and may not exceed its outer diameter. A surface of the ends of the cylindrical tip-sleeve may be streamlined. Within the catheter, the stiffness of the axial wire may exceed the stiffness of the screw wire.

BRIEF DESCRIPTION OF THE DRAWINGS

Embodiments are described in further detail below, by way of example and with reference to the accompanying drawings, in which.

DETAILED DESCRIPTION

Figure 1:
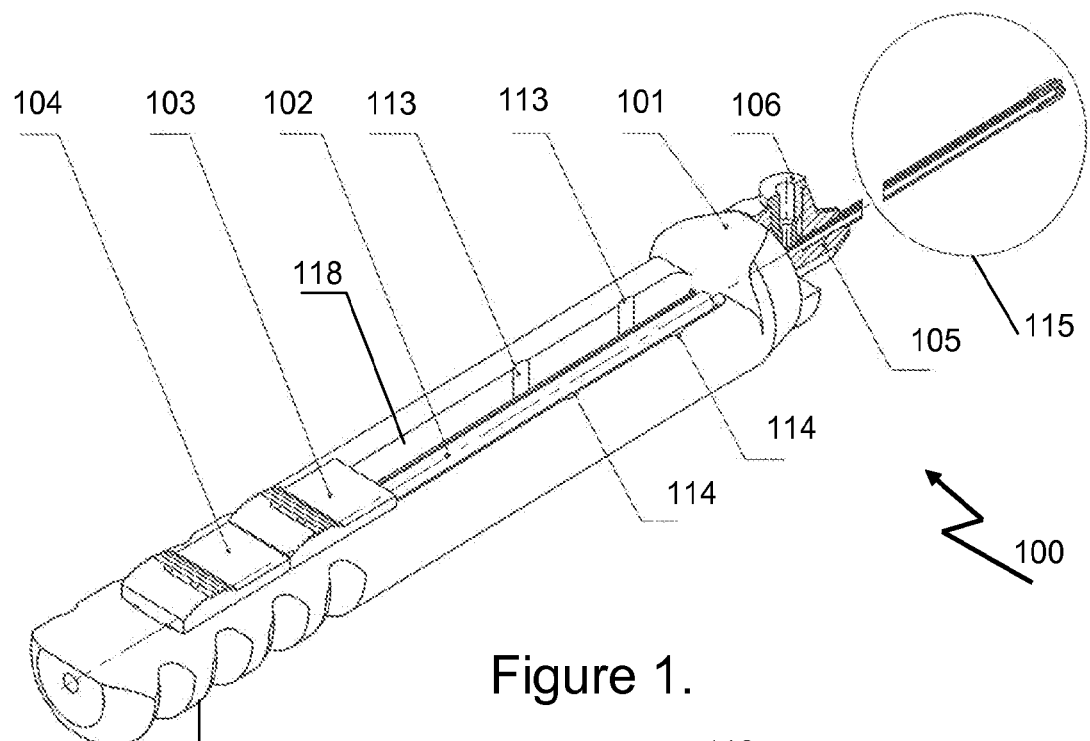
FIG. 1 is a partial cut-away perspective view of a device for retrieving a body according to some embodiments, shown with a distal end portion in a retracted state.

Described embodiments generally relate to a device for retrieving a body from a tubular structure. For example, the device may be used to retrieve an unwanted foreign or organic body within a tubular organ in a human or animal.

The device generally operates by insertion of a small diameter conduit, such as a catheter, into the tubular structure, extending past the body to be retrieved. Wire strands contained within the conduit are then extended and manipulated to form a wire trawl shape that is significantly larger in diameter than that of the conduit, thus allowing the trawl shape to be withdrawn back through the tubular structure, catching the body in the trawl shape and withdrawing the body from the tubular structure along with the conduit. Such embodiments make use of an axially extending relatively rigid metallic strand in combination with a less rigid metallic strand that is wound around the axial strand. The less rigid strand is preferably of a spiral shape and is expandable in order to form the trawl shape. Such embodiments are provided by a relatively easy to use device that allows simple manipulation and is unlikely to cause damage to sensitive tubular organs during withdrawal of the device from the body.

Referring now to FIGS. 1 to 8, a device 100 for retrieving a body or object from a tubular structure is described in further detail. The device 100 has a proximal device body 101 and a conduit 109 extending distally away from the device body 101 toward a distal end 115. The device body 101 is of a size and shape to be readily hand-held for manual manipulation of the device 100 during a procedure to retrieve the body or object. The conduit 109 has a diameter and length suitable for use with an endoscope, whereby the conduit 109 can be received in an instrument channel of the endoscope, extending in the order of one to two meters within a body as the endoscope is advanced into the body. The endoscope may provide appropriate internal imagery and control functionality in order to enable the conduit to be manipulated and placed at a suitable location within the tubular organ of the human or animal body.

The device body 101 may be shaped like a rod, with an axial channel 118 formed therein to allow axial travel of first and second actuators 103, 104 within the axial channel 118. Coupled to device body 101 at a distal end thereof is a distal end piece 105, which serves to hold and align a proximal end of the conduit 109, so that strands 107, 108 in the conduit 109 can pass into the axial channel of the device body 101 and be coupled to respective ones of the actuators 103, 104. The distal end piece 105 may be coupled to the device body 101 by a screw threaded connection, for example. The distal end piece 105 may also have a fluid inlet 106 formed in a part thereof and accessible externally, so that contrast fluid can be injected into a lumen defined by the conduit 109. Fluid inlet 106 may have a luer lock structure to mate with another luer structure for secure fluid transfer into the distal end piece 105. Further, suitable sealing may be provided to avoid or minimise fluid escape from within the end piece 105 and/or conduit 109.

Device body 101 may have gnurls, grips or other perturbations 116 along an external surface opposite the position of the actuators 103, 104 in order to assist in gripping of the device body 101 during its manipulation. While a rod-like structure is illustrated for the device body 101, it should be understood that different forms of device body 101 may be employed that are other than rod-like, while still providing the functionality described herein.

Actuators 103, 104 are axially slidable along an axial guide rod 102 that extends along and within the guide channel 118. Actuators 103, 104 are slidable separately or together, depending on the state to be adopted by the device 100. Although the guide channel 118 is illustrated as being open, a protective guard may be provided to cover over the axial guide channel 118 and conceal the axial guide rod 102. Such a protective cover may also assist in concealing and protecting the axial and spiral strands 108, 107 when they extend within the guide channel 118 when the device 100 is in the retracted state.

Conduit 109 is coupled to the device body 101 via the distal end piece 105 and extends away from the device body in a distal direction. The conduit 109 houses the axial strand 108 and the spiral strand 107, which is wound around the axial strand 108. The conduit 109 defines a lumen within which the axial and spiral strands 108, 107 extend and although there is little excess internal volume within the conduit, there remains enough space within the lumen to allow fluid flow from the fluid inlet 106 to the distal end of the conduit 109 via the space in the lumen that is not occupied by the axial and spiral strands 108, 107.

Device 100 has at a distal tip of the conduit 109 a distal end sleeve 110 within which the distal ends of the axial and spiral strands 108, 107 are fixed relative to each other. In some embodiments, the distal ends of the axial and spiral strands 108, 107 are fixed in relation to each other by clamping or crimping these two strands together. The distal end sleeve 110 has a rounded external profile in order to minimise damage to any sensitive tissue within the tubular organ or structure within which it is to extend. When the device 100 is in the retracted state, the conduit 109 may at its distal extremity abut a proximal end of the sleeve 110, so that the lumen of conduit 109 is closed at the distal end. Alternatively, the distal end of the conduit 109 may not abut the sleeve 110, thus allowing egress of contrast fluid from the distal end 115 even in the retracted state.

Figure 3:
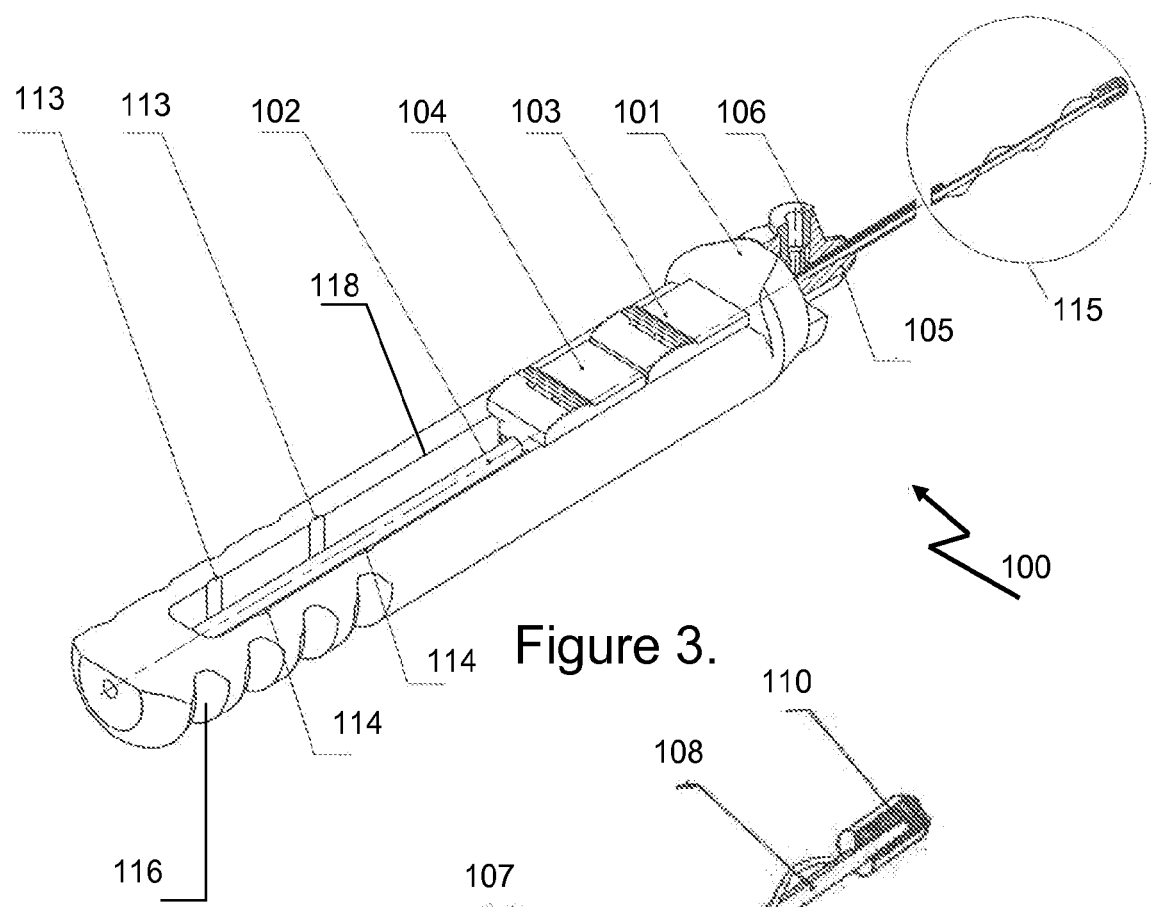
FIG. 3 is a partial cut-away perspective view of the device of FIG. 1, shown with the distal end portion in an extended state.
Figure 4:
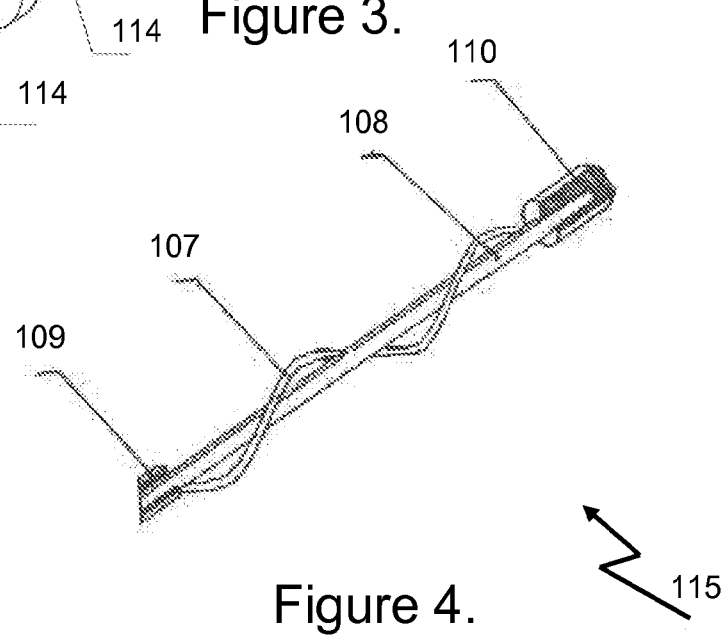
FIG. 4 is a partial cut-away perspective view of the distal end portion in the extended state.

Spiral strand 107 is coupled at its proximal end to a first actuator 103 and axial strand 108 is coupled at its proximal and to a second actuator 104. As shown in FIG. 1, the first and second actuators 103, 104 are located in their most proximal positions along the axial channel 118 of device body 101. With the first and second actuators 103, 104 thus positioned, the axial and spiral stands 108, 107 are retracted within the conduit 109. In order to retrieve a body, such as a gall stone within the gall bladder, for example, the conduit 109 is threaded along the tubular gall bladder organ past the object to be retrieved, while keeping the device in the retracted state. Once the conduit 109 is sufficiently far past the object to be retrieved, the first and second actuators 103, 104 may be pushed distally along the axial channel 118, thereby causing the axial and spiral strands 108, 107 to axially advance in the conduit 109 in a distal direction, pushing free of a distal end of the conduit 109, as shown in FIGS. 3 and 4, so that the distal end 115 of the device 100 (and the axial and spiral strands 108, 107 in particular) adopts an extended position.

Figure 5:
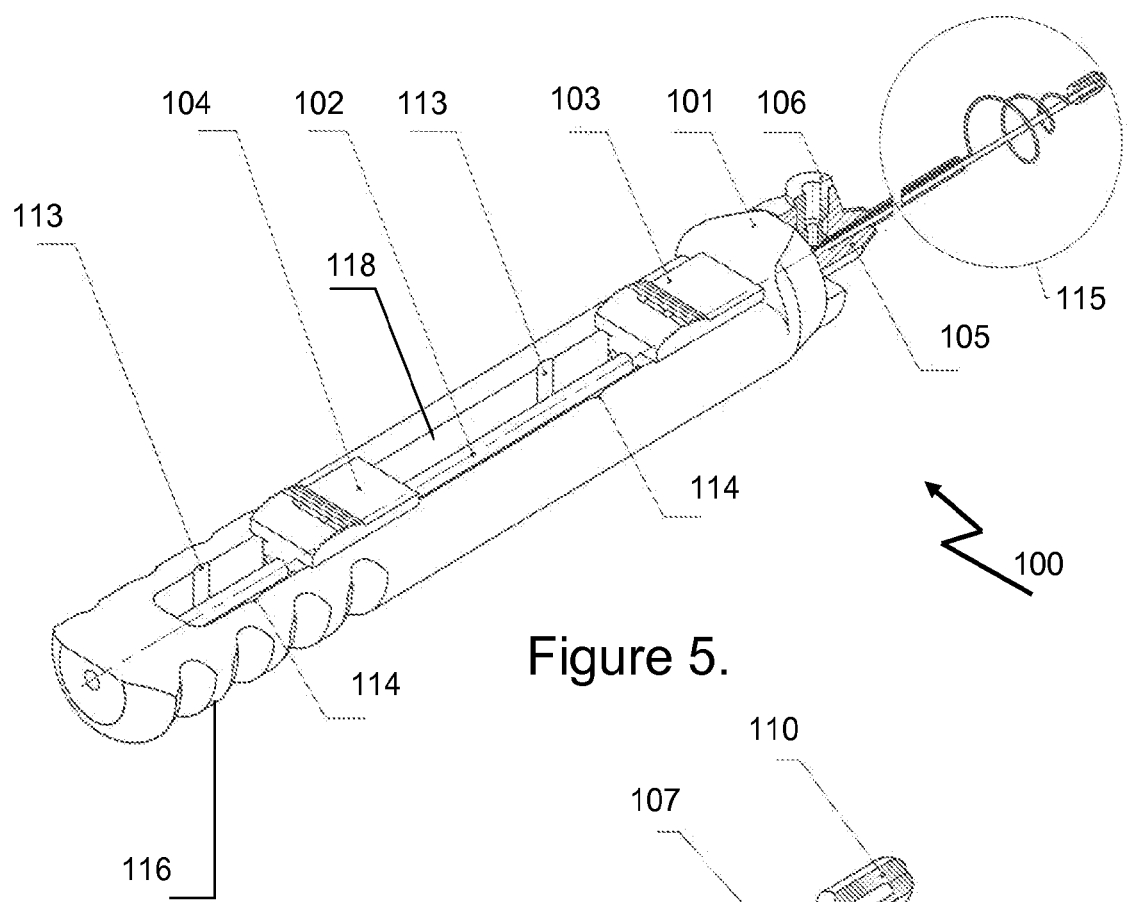
FIG. 5 is a partial cut-away perspective view of the device of FIG. 1, shown with the distal end portion in an expanded state.
Figure 6:
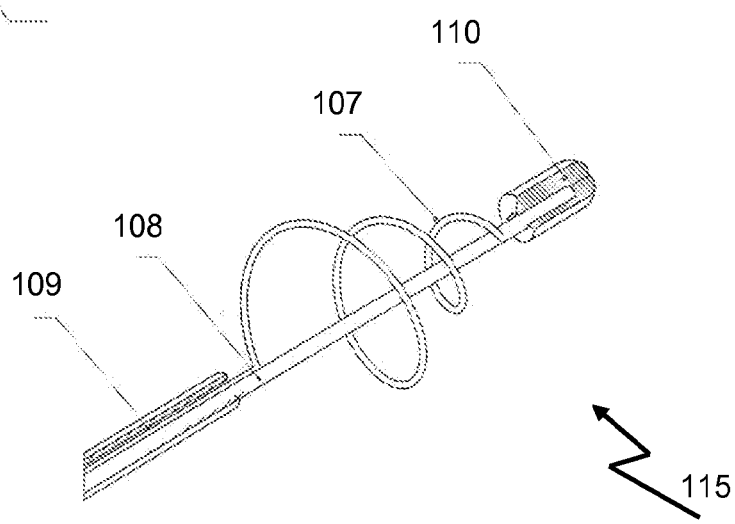
FIG. 6 is a partial cut-away perspective view of the distal end portion in the expanded state.

In order to retrieve the object, the spiral strand 107 is caused to adopt an expanded state in which it defines a trawl volume to catch the body as the distal end of the device 100 is withdrawn back through the tubular organ. The trawl volume is an open spiral strand structure that tapers radially inwardly in a distal direction, as illustrated in FIGS. 5 and 6. The spiral strand 107 is caused to adopt its expanded state by moving the second actuator 104 proximally away from the first actuator 103, thereby pulling proximally on axial strand 108 (while the first actuator remains still and spiral strand 107 maintains its position along most of its length apart from at the distal end 115) to cause relative movement between the axial and spiral strands 108, 107.

In order to have the spiral strand 107 consistently adopt a shape at the distal end 115 that defines a distally tapering trawl volume, a distal length of the spiral strand 107 is formed to have a shape memory consistent with the desired shape to be adopted in the expanded state, such as is shown in FIGS. 5 and 6, for example. For this purpose, at least a selected distal length of the spiral strand 107 is formed of a shape memory alloy such as nitinol. When the distal length of spiral strand 107 at distal end 115 is in the retracted or extended states shown in FIGS. 1 to 4, it is deformed elastically from its shape memory.

In some embodiments, spiral strand 107 may be formed of different sections, not all of which need be spiral in shape. For example, spiral strand 107 may include a straight section extending most of the length of the conduit, where it is coupled to a relatively shorter spiral section that is to be exposed and expanded to form the trawl volume. Such a straight section may or may not be formed of the same shape memory allow material as the spiral section.

In some embodiments, the axial strand 108 may also be formed of a shape memory alloy, although other bio-compatible metals may be used to form the axial strand 108. Further, it is preferred that the strands 108, 107 be formed of a metallic materials that are compatible with each other in the sense that temperature changes and internal body conditions do not cause corrosion or the generation of electrical current. For this purpose, the same metal may be used for both strands 107, 108.

Once the foreign body or the object has been withdrawn from the tubular structure by catching it in the trawl shape defined by the expanded spiral strand 107, and withdrawing the entire distal portion of the device 100 from within that tubular structure, the foreign body or object can be released within a larger tubular structure or organ for normal evacuation from the human or animal body as waste. The second actuator 104 can then be pushed distally while the first actuator 103 remains in its distal position, so that the first and second actuators 103, 104 are adjacently positioned, causing the axial strand 108 to progress distally relative to the spiral strand 107 and thereby radially contract the spiral strand 107 about the axial strand 108. This contracted state is the same as the extended state depicted in FIGS. 3 and 4, where the spiral strand 107 extends generally radially adjacent the axial strand 108. From this contracted state, both of the first and second actuators 103, 104 can be moved proximally together along the guide channel 118 to the proximal-most positions shown in FIGS. 1 and 2 to thereby cause the distal end 115 and the spiral and axial strands 107, 108 to again adopt the retracted state. Once the distal end 115 of device 100 is in the retracted state, it can be readily withdrawn from the tubular organ and/or endoscope without fear of damage to the organ.

In order to assist with transitioning the actuators 103, 104 between the different position required for the retracted, extended, expanded and contracted states, the axial guide channel 118 and actuators 103, 104 may have complimentary structures that tend to retain the actuators 103, 104 in one of two distal or two proximal positions along the axial guide channel 118. These complimentary structures can include a resiliently deflectable portion on each of the actuators 103, 104 or an internal wall of the guide channel 118, arranged to engage with a mating socket on the guide channel wall or actuators 103, 104, respectively. In the embodiment shown in the drawings, each actuator 103, 104 has resiliently deflectable bearings 111, 121 positioned on opposite sides of the actuator 103, 104 and biased outwardly by a bias mechanism 117, such as a spring. When the actuator 103, 104 is positioned so that the bearings 111, 121 mate with opposed sockets 113, 114 formed in the channel wall, the actuator 103, 104 will tend to be retained in that position unless manually pushed away from it. This biased retention of the actuators 103, 104 in either a distal or proximal position along the guide channel 118 assists in retaining the device in a desired state and minimises the risk of inadvertent contraction or retraction of the device when it is in the extended or expanded states. Further, the mating of the bearings 111, 121 with wall sockets 113, 114 provides a tactile indication to the surgical user of device 100 that the desired position of one or both of the actuators 103, 104 may have been reached.

As shown in FIGS. 1, 3, 5 and 7, the first and second actuators 103, 104 have raised portions on upper surfaces thereof in order to be readily engaged by a thumb of the user while cradling the device body 101 in the user's hand.

While embodiments are shown and described in relation to an axially oriented device body 101, it should be understood that alternative configurations of device body 101 may be employed, for example, involving differently movable actuators to cause the described relative movements of the axial and spiral strands 108, 107 with respect to each other and with respect to conduit 109. Further, while two actuators 103, 104 are shown and described, embodiments employing a different number of actuators may be employed. For example, one or three or four actuators may be employed instead of the two actuators 103, 104 described herein.

Further, some embodiments may employ more than one spiral strand 107 wound around the axial strand 108 in order to provide a more well-defined trawl volume when such plural second strands are in the expanded state. Further, the spiral strand 107 need not be wound around the entire length of the axial strand 108. Rather, the spiral strand 107 should extend spirally around axial strand 108 at least along a length of several centimetres at the distal end 115. As used herein, the term strand or wire is intended to include strands or wires made up of a single filament or multiple filaments.

An alternative description of embodiments is provided hereinafter with reference to the same drawings and incorporating language of the priority application.

Some embodiments relate to a shape memory medical device meant for extracting concrements from tubular organs, specifically stones from the ureter or bile duct. Embodiments may be used to reduce the complexity of device management and duration of medical procedures. It simplifies and improves the accuracy of device manipulation as well as increases safety of medical procedures.

The device "Trawl" contains a manipulator with an adapter installed at the output end of it. The adapter has the input and the output end: the input end contains a connection with a feeder of contrast fluid, and the output end contains a flexible catheter. Spiral and axial wires, made of shape memory alloy, are placed inside the manipulator and the flexible catheter. These wires are capable of moving along the guide axis. The top ends of the wires are fixed on the control sliders, while the bottom distal ends are fixed in a cylindrical tip-sleeve, installed outside of the free end of the flexible catheter.

The control sliders, located inside of the manipulator, are capable of joint or independent movement and fixation relative to the guide axis.

The task to be solved by the invention is to reduce the complexity in use as well as to lessen the duration of medical procedures. The invention also aims to simplify the manipulation of the device and improve the accuracy of its control, which would lead to higher safety of medical procedures.

Figure 2:
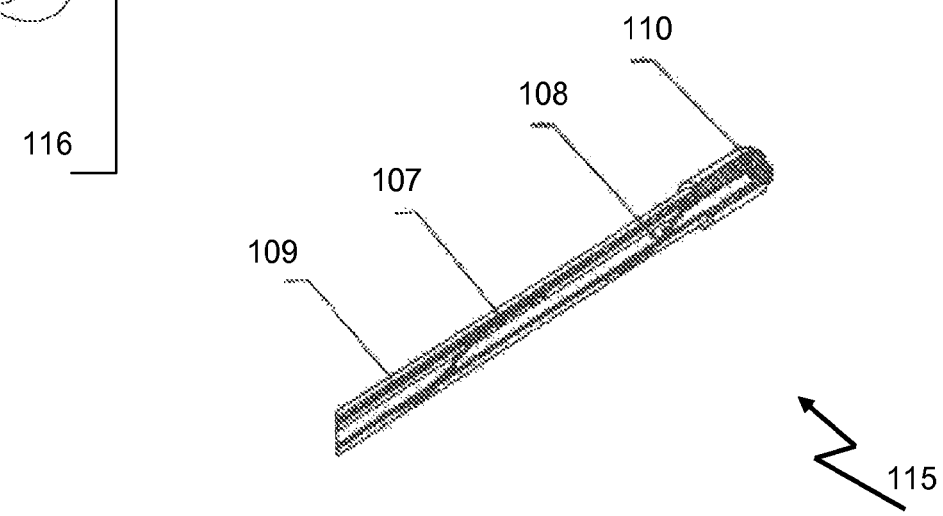
FIG. 2 is a partial cut-away perspective view of the distal end portion of the device of FIG. 1.
Figure 7:
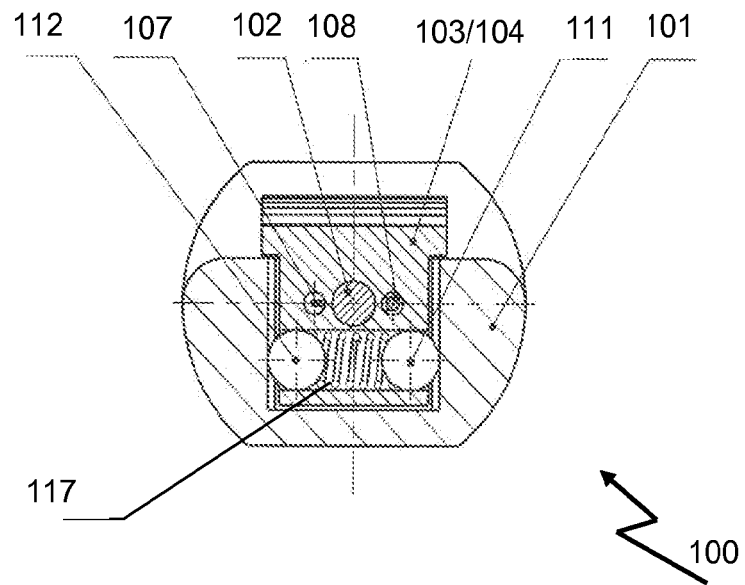
FIG. 7 is a cross-sectional view of a device body of the device of FIG. 1.

Embodiments are intended to address or ameliorate one or more shortcomings of prior instruments or to at least provide a useful alternative thereto. FIG. 1 shows a position of the device before manipulation; FIG. 2 shows a distal working portion of the device from FIG. 1 before manipulation (incision A); FIG. 3 shows the device prepared for entering a hollow organ with sliders being positioned before capturing a concrement; FIG. 4 shows the device (incision A) once it has entered into a hollow organ before capturing a concrement; FIG. 5 shows the device once it has entered into a hollow organ and ready to capture a concrement; FIG. 6 shows the distal portion of the device, with a spiral wire fully extended to capture a concrement; FIG. 7 shows a section of the device illustrating movement and fixation of the sliders, corresponding to the position of the device shown in FIG. 5.

Embodiments generally relate to a device for removing bodies, such as concretions, concrements or foreign bodies from tubular structures, such as tubular organs in a human or animal. Embodiments may allow a simplified manipulation, thereby reducing complexity to the surgical user, which may in turn reduce the duration of medical procedures and may increase the accuracy of the instrument, which may lead to improved safety and/or efficacy for medical procedures of this nature.

There are a number of tubular organs within a human or animal body, to which described embodiments could be applied to retrieve an unwanted or troublesome body, such as in bile ducts, ureter, tracheae, oesophagus, blood vessels and intestines, for example. Although embodiments are discussed in relation to procedures to be carried out on human patients, the described embodiments are believed have equal potential for application to animals and other sensitive, organic tubular organs.

FIGS. 1 to 8 illustrate a device 100 "Trawl" for extracting foreign bodies from tubular organs. The device 100 comprises a manipulation tool 101, which forms a proximal body of the device 100, and an operational tool 115, which forms a distally extending trawling component of the device 100. The manipulator 100 is equipped with an adapter 105 installed at an output end. The manipulator 100 is further comprised of a series of circular grooves 116 at the proximal end to aid with grip and manipulation of the manipulator 100 by a surgeon. A sleeve is connected to a contrast fluid feeder, which is located at the input end of the adapter 105 at the connection point 106 and an elastic catheter 109 is positioned at the output end of the adaptor 105.

A spiral wire 107 and an axial wire 108 are located inside a manipulator frame 101 and the flexible catheter 109. Both wires being made from a shape-memory alloy. These wires are able to move along a guide axis 102 within the manipulator frame 101. These wires are able to move along the guide axis 102. The ends of these wires 107/108 are fixed on control sliders 103/104, and opposed distal ends are fixed inside a cylindrical tip-sleeve 110 installed outside the free end of the flexible catheter 109. Control sliders 103/104 are located in the frame 101 and are capable of joint or independent movement and fixation relative to the guide axis 102. The axial wire 108 is located inside the cone of the elastic catheter 109, which is formed by the spiral wire 107.

The proximal end of spiral wire 107 is permanently affixed to an upper control slider 103 and the proximal end of the axial wire 108 is permanently affixed to a lower control slider 104. The distal ends of both wires 107/108 are rigidly attached inside a cylindrical tip-sleeve 110 which is located at the distal, free end of the flexible catheter 109. The control sliders 103/104 are located in the manipulator frame 101 and are capable of coincident or independent movement and fixation along the slider guide axis 102. The axial wire 107 and the spiral wire 108 are located inside the flexible catheter 109 wherein the spiral wire 108 is wound around the axial wire 107 forming a coiled outer layer around the axial wire 107.

The spiral wire 108 and axial wire 107 are made of nitinol, a Nickel-Titanium (NiTi) shape-memory alloy, although other shape-memory alloys may be employed instead.

Nitinol offers a favourable combination of physical and mechanical properties. Aside from its biocompatibility (a similar corrosion resistance to that of stainless steel), it is flexible (low Young's modulus of about 75 GPa), has a high UTS (about 750-960 MPa), displays biased stiffness characteristics (stiff in compressions and flexible in tension) and displays its super-elastic behaviour in a similar temperature range to the human body. In these properties it combines many of the advantages of a metal and a plastic into one material, allowing it to be forcibly pushed into position with minimal risk of kinking When the wires 107 and 108 are inside to the body, the application of heat will trigger the shape memory effect, assisting in forming the desired helical form to trap a concrement. The specific properties of Nitinol and other shape-memory alloys offer superb elasticity and restorative properties to assist in achieving the desired form in the spiral wire 108.

The ability to form the appropriate helical profile is necessary to deal with the variety of concrements that may need to be removed from the tubular organs. Some are hard and unyielding, however some may be soft and malleable. Some embodiments of wire trap may apply undue pressure to the concrement, causing it to deform and mould itself around the wire. In this situation the surgeon may be unable to release the concrement or fully retract the catheter 109, causing potential trauma to the tubular organ. In a preferred embodiment, the spiral wire 108 is given its shape-memory form as a helical coil, reducing the likelihood of uneven pressure being applied to a concrement thus reducing the risk of entangling the concrement and the spiral 108 and axial wires 107.

The movement and fixation of the control sliders 103/104 are achieved with the help of two spring-loaded balls 111/112, set symmetrically along the guide axis 102, and a pair of grooves 113/114 on the inner side of the frame 101.

FIG. 7 shows the securing of the upper 103 and lower control sliders 104 which is achieved using a pair of spring-loaded balls 111/112 for each slider. The balls 111/112 are imbedded within the surface of each individual slider, diametrically opposed either end of a spring 117. The spring 117 is used to place a tensioning force on the inner surface of each of the balls 111 and 112. The tensile force applied to the balls 111 and 112 is used to lock them in place, so that when the balls 111 and 112 align with the respective locking holes 113 and 114. The locking holes 113 and 114 are set symmetrically along the slider guide axis 102 along the length of the slider track 118 within the manipulator frame 101. The balls 111/112 can be disengaged from their locked position, using only a force applied by the surgeon's hand, this provides a gentle action and ease of use.

Distal ends of the spiral 107 and axial wires 108 are securely mounted in the longitudinal channels of the cylindrical tip-sleeve 110. The mounting is achieved via pressing direct martensitic transformation in the material of both wires 107/108 in the set temperature range.

Figure 8:
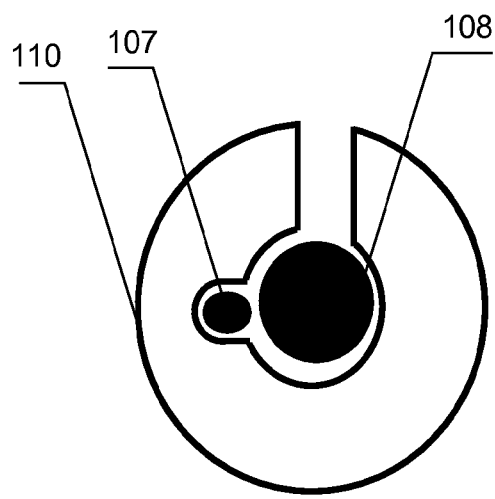
FIG. 8 is a schematic cross-sectional view of a distal tip of the device of FIG. 1.

The mounting is formed by directly crimping the wires 107/108 at a temperature within the martensitic transformation range of the shape-memory alloy, as shown in FIG. 8.

The winding tension of the spiral wire 107 around the axial wire 108 is important. The longitudinal distance between the turns of the spiral wire 107 does not exceed the arithmetic mean of the radius of the adjacent turns.

This ratio provides a gradual increase in the helical coil of the spiral wire 107 and minimises the opportunity for a concrement to slip between the turns of the spiral wire 107.

The surface of the cylindrical tip-sleeve's end 110 is streamlined to achieve a trauma free shape.

FIG. 8 illustrates a cross-section of the cylindrical tip-sleeve 110, the surface of the end of which is streamlined to achieve a trauma free shape on ingress and egress of the operational tool 115. The tip-sleeve end 110 has a rounded shape, and the cross-sectional drawing shows the internal crimping mechanism used to secure the ends of the spiral wire 107 and axial wire 108. The tip-sleeve 110 is shown in FIGS. 2, 4 and 6 as a pellet shape; wherein the distal end is closed and the proximal end is open, to receive the two wires 107 and 108. For tip-sleeve 110, a streamlined and smooth surface finish is preferred and minimal, if any, sharp radii are desirable, as these may increase trauma to the tubular organ on ingress and egress. A bulb shaped tip-sleeve 110 has also been contemplated, whereby the maximum circumference of the tip-sleeve 110 is at a central point along the longitudinal axis of the tip-sleeve and the circumference of the tip-sleeve reduces in both directions along the longitudinal axis from the maximum point. This embodiment provides a tip-sleeve with a distal end that is a solid bulb and a proximal end (where the wires 107 and 108 enter the tip-sleeve) of lesser circumference than the maximum circumference of the tip-sleeve. This shape minimises trauma to the tubular organ both in forwards and rearwards travel of the tip-sleeve 110.

The cross-section shown in FIG. 8 illustrates a generally circular section, with a straight channel cut from the external surface of the tip-sleeve 110, with an adjacent central cavity formed within the tip-sleeve 110. The straight channel is positioned eccentrically on the tip-sleeve 100 cross-section although it is contemplated that different locations for the straight channel may be configured. The straight channel facilitates the insertion of the wires 107 and 108 into the tip-sleeve 110 prior to the crimping operation. The central cavity is formed with a cross-section resembling two overlapping circles of different diameters. The smaller diameter cavity section is sized to receive the smaller gauge wire, generally the spiral wire 107, while the larger diameter cavity is sized to receive the larger gauge wire, generally the axial wire 108. Once the distal ends of both wires 107 and 108 have been slid through the straight channel and located within their respective cavities, an inward force is applied circumferentially to the external surface of the tip-sleeve 110, internally deforming the cavities and thus trapping and crimping the ends of both wires 107 and 108. The wires are then affixed both to each other and to the tip-sleeve 110. In order to further improve the strength of this connection a series of small undulations, or teeth or nubs may be formed in the internal surfaces of the tip-sleeve 110 internal cavities. These teeth serve to increase friction and thereby grip, however, they are not shown in FIG. 8.

Crimping the two wires 107 and 108 is a very reliable method of joining the two wires and also a reliable method of securing the tip-sleeve 110. Crimping is a cheap, reliable and efficient method of joining Nitinol wires and minimises the risk of disconnection during use, which would have serious implications for the patient. However, other embodiments may employ a different means of affixing the distal ends of spiral and axial wired 107, 108 relative to each other and need not cause direct contact between the two wires, provided there is minimal risk of the wires coming loose.

The stiffness of the elastic catheter's axial wire 108 exceeds the stiffness of the spiral wire 107.

To achieve the stiffness differential using the same material the axial wire 107 is of a heavier gauge than that of the spiral wire 108 ensuring that the stiffness (resistance to deformation) of the axial wire 108 exceeds the stiffness of the spiral wire 107.

The outer diameter of the cylindrical tip-sleeve 110 is at least equal to the inner diameter of the flexible catheter 109 and does not exceed its outer diameter.

This ensures that the tip-sleeve 110 is large enough that it cannot be retracted into the flexible catheter 109 and is small enough to be fed through the flexible catheter 109. The flexible catheter 109 is about 1 mm to 7 mm in diameter, depending on the procedure to be carried out and the relative size of the organ to be entered.

The device "Trawl" includes (FIG. 1-6) a manipulator with the frame 101, an axial guide 102 for the spiral wire 107 and the axial wire 108, both mounted inside the frame 101 and made from a shape memory alloy, such as nitinol, thermally treated for super elasticity. If a different material is used, which does not possess super elasticity, the device will be not be operating.

The wires 107/108 may be made from a shape memory alloy, such as Nitinol, thermally treated for super elasticity; however other shape-memory alloys may be used in place of Nitinol.

The proximal end of axial wire 108 is fixed inside the slider 104, while the proximal end of the spiral wire 107 is fixed inside a different slider 103.

In a preferred embodiment the proximal end of axial wire 108 is fixed inside a lower slider 104, while the proximal end of the spiral wire 107 is fixed inside an upper slider 103.

The adapter 105 is installed at the output end of the frame 101. The adapter hosts a connection 106, with the feeder of contrast fluid (not shown in the drawing) installed at the input end of the adapter. A syringe can easily be used as a feeder of the contrast fluid.

Figure 9:
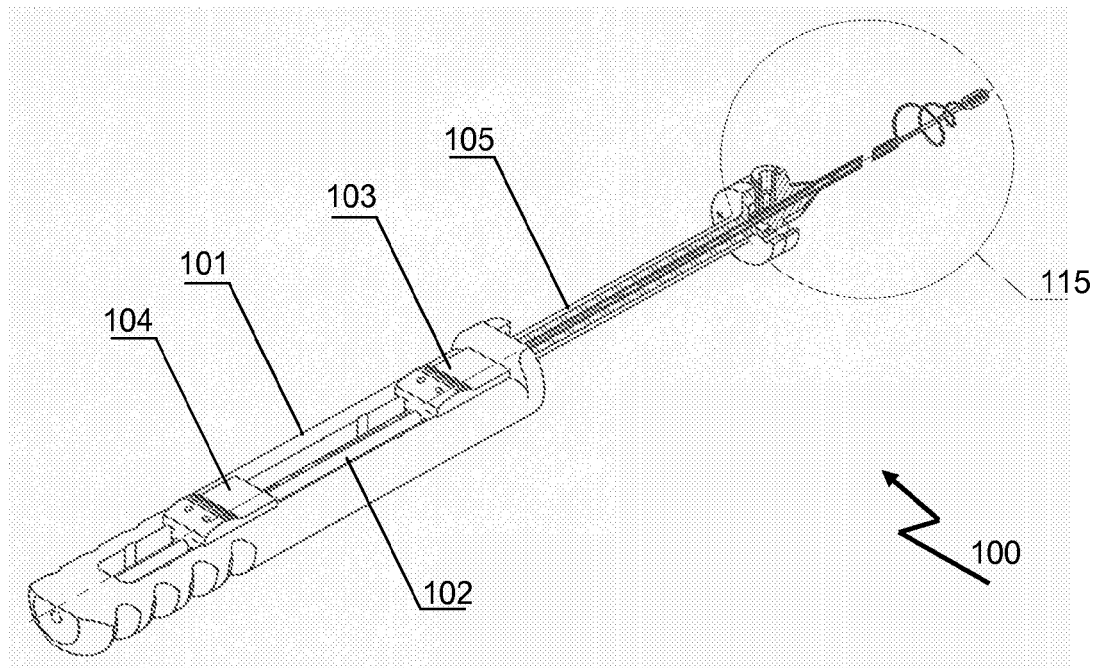
FIG. 9 is a partial cut-away perspective view of a device according to further embodiments, including a semi-rigid distal extension of the device body, where a connection point for fluid ingress to the catheter is positioned at a distal portion of the extension.
Figure 10:
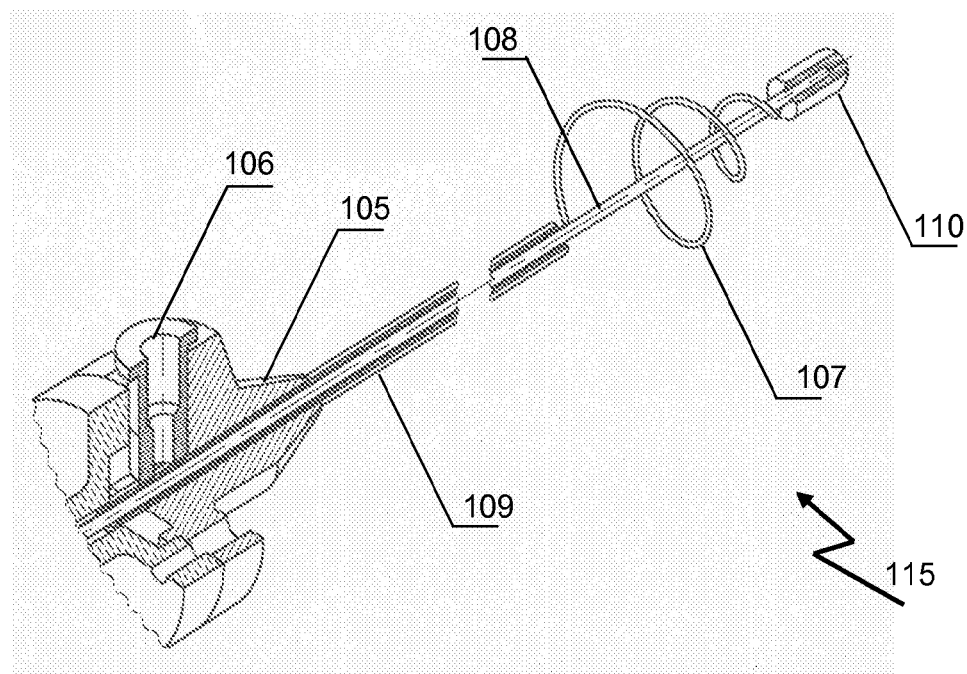
FIG. 10 is a partial cut-away perspective view of a distal end portion of the device of FIG. 9.

The adapter 105 is installed at the distal end of the manipulator frame 101, and may have a body of varying length. FIG. 9 illustrates an embodiment of the device 100, where the adaptor 105 is extended, to effectively increase the rigid body portion 101 of the device 100 and extend the location of the connection point 106 from the device frame 101. The adapter 105 hosts a connection 106, for a feeder of contrast fluid (not shown in the drawing) installed at a point on the adapter 105 body. A syringe or other similar device may then be used as a feeder of a contrast fluid for the desired procedure. The contrast fluid flows through the flexible catheter 109 and is released into the body proximate the tip-sleeve 110, where the contrast fluid there aids the surgeon by improving visibility of the operation site. The adaptor 105 need not be directly connected to the manipulator frame 101, as long as there are manual controls for the wires 107 and 108 provided for between the manipulator frame 101 and the adaptor 105.

The flexible catheter 109 is attached to the output end of the adapter 105. The wires 107 and 108 are partially located inside the catheter 109 and are capable of axial movement.

The wires 107 and 108 are capable of movement relative to each other and may also be manoeuvred through the catheter 109 together by applying pressure to the manipulator frame 101.

The distal ends of the wires 107 and 108 are connected with the cylindrical tip-sleeve 110 installed at free end of the flexible catheter 109.

The connection between the distal ends of the wires 107 and 108 is permanently affixed into the cylindrical tip-sleeve 110 located at the distal (free) end of the flexible catheter 109.

Sliders 103 and 104 are located in the frame 101 and are capable of joint or independent movement and fixation relative to the guide axis 102 of the frame 101. The mechanism of movement and fixation of the sliders 103 and 104 is made of the two spring-loaded balls 111 and 112, set symmetrically to the guide axis 102 and a pair of grooves 113 and 114, set on the internal wall of the frame 101 as illustrated by FIG. 7.

Upper slider 103 and lower slider 104 are positioned within the frame 101 and are free to move together or independently. They are also capable of being jointly or independently relative to the slider guide axis 102 of the manipulator frame 101. The locking mechanism of the sliders 103 and 104 is comprised of two spring-loaded balls 111 and 112, symmetrically aligned to the slider guide axis 102. The slider guide axis 102 has a series of pairs of grooves 113 and 114, located on the internal walls of the manipulator frame 101 as illustrated by FIG. 7. This allows the sliders 103 and 104 to be locked in position at multiple points along the slider track 118.

This mechanism of movement and fixation of the sliders 103 and 104 provides tangible control of the position of these sliders: the extreme position of the sliders can be felt well tacitly (tactilely) when the balls 111 and 112 of the sliders are in the holes 113 and 114. In addition, this mechanism also provides a sound control: when the balls 111 and 112 are locked in the holes 113 and 114, they click.

The control mechanism of the sliders 103 and 104 provides delicate control and indication of the position of the sliders: the extremities of the positions of the sliders can be felt by the surgeon as the balls 111 and 112 in the sliders 103/104 align and spring into corresponding grooves 113 and 114. In addition to being able to feel the locking of the balls 111/112, this mechanism also provides a sound indicator as the balls 111 and 112 make an audible "click" upon locking into grooves 113 and 114.

The surgeon is able to manipulate the trawl 100 by looking at a monitor screen of an X-ray machine, which contributes to better focus on the proper course of surgery.

The tactile feedback and engagement sounds of the device 100 are used as a guide for the surgeon however the position of the tip-sleeve 110 and wires 107/108 within the tubular organ, relative to the concrement, is verified and adjusted from the x-ray images as seen on the x-ray monitor.

The distal ends of the wires 107 and 108 are installed in the longitudinal channels of the cylindrical tip-sleeve 110 via pressure crimping. The use of this technique allows the cohesive force to significantly exceed the capability of the existing analogues inventions. The results of tests carried out on a tensile testing machine, showed that tensile force, which is capable of maintaining the connection, is 16.2 kN. This force is seven times greater than that of the existing inventions.

The pressure crimping of both wires 107/108 inside the tip-sleeve 110 is conducted in a temperature range of direct martensitic transformation (+25 to $-20°$ C.). Thus the required efforts to operate the device are relatively minor. When the material reaches the temperature of the human body, it develops a reactive pressure of up to 500 MPa achieving extremely reliable fixation of the ends of the wires inside the tip-sleeve 110. Such technology ensures the reliability of the device in operation and prevents patient injury during surgeries. Where the two wires 107/108 are not firmly attached and the connection between them is severed trauma to the tubular organ may be caused. This is also possible if the tip-sleeve 110 is not suitably rounded or streamlined which can cause trauma when manoeuvring through the tubular organ, increasing the possibility of catching or tearing at any internal folds within the organ.

In the operating mode the longitudinal distance between the turns of the screw wire 107 will not exceed the arithmetic mean of the adjacent turns' radii, which prevents a concrement captured by the Trawl 100 to be lost. It also limits the undue expansion the wires. In particular undue expansion of the spiral wire 107.

The outer diameter of the cylindrical tip-sleeve 110 is at least equal to the inner diameter of the flexible catheter 109 and does not exceed the catheter's outer diameter. These specifications allow the tip-sleeve 110 to always remain outside of the catheter 109. In other embodiments the outer diameter of the tip-sleeve 110 is at least equal to the inner diameter of the catheter 109, and may be larger than that of the outer diameter of the catheter 109 providing a rounded or bulbous tip-sleeve profile. The maximum diameter of the tip-sleeve 110 must be less than that of the endoscope, if the device 115 is to be inserted into the tubular organ through an endoscope and to travel freely within the channel of the endoscope.

In a preferred scenario the device 115 is not introduced into the tubular organ alone, but is instead inserted through an endoscope already correctly positioned within the tubular organ. To minimise trauma to a patient an endoscope may be left in position and used for the ingress and egress of several medical instruments to facilitate multiple complimentary procedures.

The ends of the cylindrical tip-sleeve 110 are streamlined, which allows for trauma free entry of the device 115 into hollow organs.

The tip-sleeve 110 is the most likely component to cause trauma to a patient, both on ingress of the device and egress, and further while travelling along tubular organs where there is a potential for the tip-sleeve to catch if not appropriately shaped.

The stiffness of the axial wire 108 exceeds the stiffness of the spiral wire 107 to allow the device to transition from the position described in FIGS. 1 and 2 to the position in FIGS. 3 and 4.

The device "Trawl" works as follows:
Position 1. Both control sliders 103 and 104 are in the proximal position: leftmost position in FIG. 1. Both wires 107 and 108 are located inside the catheter 109.

Both wires 107 and 108 are located fully inside the catheter 109 and manipulator 100 in position 1.

Position 2. Both sliders 103 and 104 are pushed into the distal position: rightmost position in FIG. 1. Both wires 107 and 108 are brought out of the catheter, while the spiral wire 107 is widely stretched.

Position 2 is shown in FIGS. 3 and 4, where both sliders 103 and 104 have been pushed into a maximum distal position, at the top end of the manipulator 100. In this position both wires 107 and 108 have been pushed out of the distal end of the catheter 109, while the spiral wire 107 remains coiled around the axial wire 108.

Position 3. The control slider 104 is partially moved back to the proximal, but not the extreme position by the axial wire 108: an intermediate left position in FIG. 5. At the same time the spiral wire 107 is forming a spiral trawl-trap.

Position 3 is shown in FIGS. 5 and 6, where the control slider 104 has been partially moved back towards the proximal end of the manipulator 100 and where the upper slider 103 has been left in the extreme distal position on the manipulator 100. These slider 103/104 movements have caused the axial wire 108 to retract, while leaving the spiral wire 107 at its fully extended length, thus repositioning the two wires 107 and 108 relative to each other and forming a spiral trawl-trap, as shown in detail in FIG. 6.

The device is brought into Position 1. To do this, the slider 103 is pressed, which leads to both sliders 103 and 104 being pushed back, i.e. the extreme left or proximal position on FIG. 1. Working part of the trap is moved back into the catheter 109. A surgeon can feel the fixation of the device in the Position 1 tacitly, as confirmed by the click of the balls 111 and 112 moving into the holes 113/114.

To bring the device into Position 1, the upper slider 103 is pressed and pulled down towards the proximal end of the manipulator 100. This causes both sliders 103 and 104 to be pushed backwards, i.e. the position in FIG. 1. The working part of the trap i.e. the spiral wire 107 is pulled back into the flexible catheter 109. A surgeon can feel the movement of the axial 108 and spiral wire 107 tacitly through the upper and lower sliders 103/104, and the motion is confirmed by the audible click of the balls 111 and 112 as they move and lock into the holes 113 and 114.

The device is brought into Position 2. To do this, the slider 104 is pressed, which leads to both sliders 103 and 104 being pushed forward (right). At the same time the working part of the device is advancing from the catheter 109 and moving towards a concrement. A surgeon can feel the fixation of the device in the Position 2 tacitly, as confirmed by the click of the balls 111 and 112 moving into the holes 113/114.

The device is brought into Position 2 by pressing the slider 104 forwards towards the distal end of the manipulator 100 which causes both sliders 103 and 104 to be moved to the distal position. This slider motion extends the operational tool 115 of the device from the catheter 109, moving it towards a concrement to be removed. Depending on the concrement location and size, it is possible that the tip-sleeve 110 will need to be extended past the concrement within the tubular organ, in order to facilitate capture of said concrement. A surgeon can physically feel the location of the operational tool 115 as it reaches Position 2. This location is also confirmed by the audible click of the balls 111 and 112 moving into the locking holes 113 and 114.

The device is brought into Position 3. A surgeon can feel the fixation of the device in the Position 3 tacitly, as confirmed by the click of the balls (11) and (12) moving into the holes (13)—one before far left. At the same time as the axial wire (8) is moved by the slider (4), the spiral wire (7) is forming a spiral trawl-trap. A concrement is captured into the basket by pulling the catheter (9). Then a concrement is pulled into the channel of the endoscope, which is extracted out.

The device is brought into Position 3 by moving slider 104 back towards the proximal end of the manipulator 100. The tip-sleeve 110 at this time is in a position behind the concrement, having been extended past the concrement when inserted in to the tubular organ. Moving slider 104 retracts the axial wire 108 (individually controlled by the slider 104), and the excess length of the spiral wire 107, relative to the shortened axial wire 108, begins to form a spiral trawl-trap centred around the taught axial wire 108. A concrement may be captured by the trawl-trap by gently manoeuvring the catheter 109 so the tubular organ becomes blocked by the trawl-trap.

The captured concrement is then positioned in front of the trawl-trap and may then be pulled or trawled out of the tubular organ in a direction towards the flexible catheter 109. The concrement is gently trawled from the tubular organ until a junction is found with a larger organ, such as the intestine, where the concrement is then gently guided into the larger organ. From this position the body will naturally dispose of the concrement having removed the capacity for the concrement to block the smaller tubular organ. The device 115 is then retracted from the organ (or endoscope). A surgeon will physically feel the movement of the device into Position 3 through contact with the slider 104, and as before the locking mechanism of the slider will be confirmed by an audible click of the balls 111 and 112 moving into the locking holes 113 and 114.

If a concrement cannot be retrieved, it can be released without injuring a patient. To do this, the device is moved into Position 2. The spiral wire 107 is extended as it moves in front of the axial wire 108 and a concrement is released.

If a concrement cannot be removed successfully from the organ, it can be released causing minimal trauma to the patient. To do this the above process is performed in reverse. The device is moved back into position 2 by moving slider 104 back towards the distal end of the manipulator 100. This extends the axial wire 108 in a direction away from the open end of the catheter 109, pulling the spiral wire 107 back into a closely coiled formation around the axial wire 108 and thus releasing the captured concrement. Although the wires 107 and 108 have assumed their shape-memory form due to the temperature change in the tubular organ, the mechanical force applied by the sliders 103 and 104 is sufficient to return the super elastic wires 107 and 108 back to their original, compact form and position to be retracted back into the flexible catheter 109.

The device is brought into Position 1 (FIGS. 1 and 2). To do this, the slider 103 is pressed on and both sliders 103 and 104 move back into the proximal (left) position. The working part of the trap is moved into the catheter 109 and the device is extracted.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A device for retrieving a body from within a tubular structure, the device having a proximal end and a distal end and comprising:
a device body at the proximal end, the device body defining a guide channel;
a conduit extending away from the device body to the distal end and sized to be receivable in the tubular structure;
at least one actuator operably associated with the device body, the at least one actuator comprising a first actuator and a second actuator, wherein the first and second actuators are separately operable;
a first strand extending at least in part through the conduit;
a second strand extending at least in part through the conduit;
wherein the first and second strands are affixed at the distal end of the device, and wherein the second strand is wound around the first strand along at least a distal length of the first strand;
wherein moving the first actuator proximally away from the second actuator causes the second strand to adopt an expanded state in which the second strand defines a trawl volume to catch the body for retrieval of the body from the tubular structure;
wherein at least one of the first actuator and the second actuator is moveable relative to the device body within the guide channel, and has at least one engagement portion to engage with at least one complementary structure of the channel, such that when the at least one engagement portion is engaged with the at least one complementary structure, the at least one of the first actuator and the second actuator are caused to be retained in place relative to the device body by the engagement portion; and
wherein the first strand is coupled to the first actuator and the second strand is coupled to the second actuator, whereby relative movement between the first and second actuators causes relative movement between the first and second strands, and wherein the first actuator is movable in an axial direction to cause axial movement of at least a proximal end of the first strand and the second actuator is movable in a proximal direction to cause proximal movement of at least a proximal end of the second strand.

2. The device of claim 1, wherein the trawl volume is defined by a spiral shape of the second strand in the expanded state.

3. The device of claim 1, wherein the trawl volume tapers inwardly toward the first strand in a direction toward the distal end.

4. The device of claim 1, wherein the second strand is formed of a shape-memory alloy along at least a distal length of the second strand.

5. The device of claim 4, wherein the distal length of the second strand is formed to have a shape memory that defines the trawl volume.

6. The device of claim 1, wherein in the expanded state, the second strand extends radially beyond an outside diameter of the conduit.

7. The device of claim 1, wherein relative movement between the first actuator and the second actuator causes the second strand to adopt a contracted state in which the second strand extends radially adjacent the first strand.

8. The device of claim 1, wherein the first strand has a larger diameter and stiffness than a diameter and stiffness of the second strand.

9. The device of claim 1, further comprising a distal tip sleeve located at a distal extremity of the device, the distal tip sleeve receiving distal ends of the first and second strands, wherein the distal tip sleeve has a diameter greater than or equal to a diameter of the conduit.

10. The device of claim 9, wherein the distal tip sleeve retains the distal ends of the first and second strands in fixed relation to each other by clamping or crimping them together.

11. The device of claim 9, wherein the distal tip sleeve has a rounded external profile.

12. The device of claim 1, wherein relative movement between the first actuator and the second actuator causes the first and second strands to adopt a retracted state in which distal lengths of the first and second strands are substantially enclosed within the conduit, wherein in the retracted state, the conduit obstructs the second strand from adopting the expanded state.

13. The device of claim 1, wherein relative movement between the first actuator and the second actuator causes the first and second strands to adopt an extended state in which distal lengths of the first and second strands are substantially uncovered by the conduit, wherein in the extended state, the conduit does not obstruct the second strand from adopting the expanded state.

14. The device of claim 1, wherein the second strand is caused to adopt the expanded state in response to relative movement between the first and second actuators.

15. The device of claim 1, wherein the at least one engagement portion and the at least one complementary structure comprises a resiliently deflectable portion and a mating socket, wherein manual force can be applied to remove the resiliently deflectable portion from the mating socket.

16. The device of claim 1, wherein at least one of the first actuator and the second actuator is slidably moveable relative to the device body.

17. The device of claim 1, wherein the conduit defines a lumen within which the first and second strands extend, the lumen and the first and second strands being sized to allow flow of fluid through the lumen toward the distal end.

18. The device of claim 17, further comprising a fluid inlet arranged on the device body, the fluid inlet in fluid communication with the lumen to allow contrast fluid to be passed from the fluid inlet to the distal end via the lumen.

19. The device of claim 1, wherein the conduit is sized to be receivable within an instrument channel of an endoscope.

20. The device of claim 1, wherein the first and second strands are metallic strands formed of bio-compatible materials.

21. Use of the device of claim 1 to retrieve a body from a tubular structure.

* * * * *